(12) United States Patent
Kapadia

(10) Patent No.: US 10,390,853 B2
(45) Date of Patent: Aug. 27, 2019

(54) ROBOTICALLY CONTROLLING MECHANICAL ADVANTAGE GRIPPING

(71) Applicant: Covidien LP, Mansfield, MA (US)

(72) Inventor: Jaimeen Kapadia, Bridgeport, CT (US)

(73) Assignee: Covidien LP, Mansfield, MA (US)

(*) Notice: Subject to any disclaimer, the term of this patent is extended or adjusted under 35 U.S.C. 154(b) by 199 days.

(21) Appl. No.: 15/502,297

(22) PCT Filed: Jul. 22, 2015

(86) PCT No.: PCT/US2015/041442
§ 371 (c)(1),
(2) Date: Feb. 7, 2017

(87) PCT Pub. No.: WO2016/025134
PCT Pub. Date: Feb. 18, 2016

(65) Prior Publication Data
US 2017/0224367 A1  Aug. 10, 2017

Related U.S. Application Data

(60) Provisional application No. 62/036,904, filed on Aug. 13, 2014.

(51) Int. Cl.
*A61B 17/00* (2006.01)
*A61B 17/29* (2006.01)
(Continued)

(52) U.S. Cl.
CPC ............. *A61B 17/29* (2013.01); *A61B 34/30* (2016.02); *A61B 34/35* (2016.02); *A61B 34/71* (2016.02);
(Continued)

(58) Field of Classification Search
CPC ......... A61B 17/29; A61B 34/30; A61B 34/35; A61B 34/71; A61B 34/74; A61B 90/37;
(Continued)

(56) References Cited

U.S. PATENT DOCUMENTS

| 5,207,114 A | 5/1993 | Salisbury, Jr. et al. |
| 5,382,253 A | 1/1995 | Hogendijk |

(Continued)

FOREIGN PATENT DOCUMENTS

| EP | 2687177 A2 | 1/2014 |
| JP | 2006-061364 A | 3/2006 |

(Continued)

OTHER PUBLICATIONS

International Search Report for (PCT/US2015/041442) date of completion is May 12, 2016 (3 pages).

(Continued)

*Primary Examiner* — Katrina M Stransky

(57) ABSTRACT

An end effector of a surgical tool may include a housing, a jaw support shaft, jaw members, an articulation member, and cam pulleys. The jaw members may be supported on the support shaft and may be pivotable about a pivot axis. The articulation member may have a slot and include articulation pins extending from it that are coupled to the jaw members. The slot may be adapted to receive the jaw support shaft to support the articulation member between the jaw members. The articulation member may be rotatable about the jaw support shaft to articulate the jaw members relative to the longitudinal axis. The cam pulleys may be mounted to the housing and coupled to the jaw members. The cam pulleys may be rotatable about the pivot axis to pivot the pair of jaw members between open and closed conditions.

20 Claims, 9 Drawing Sheets

(51) Int. Cl.
*A61B 34/00* (2016.01)
*A61B 34/30* (2016.01)
*A61B 34/35* (2016.01)
*A61B 90/00* (2016.01)

(52) U.S. Cl.
CPC .............. *A61B 34/74* (2016.02); *A61B 90/37* (2016.02); *A61B 2017/00398* (2013.01); *A61B 2017/2936* (2013.01); *A61B 2017/2938* (2013.01); *A61B 2034/305* (2016.02)

(58) Field of Classification Search
CPC ........ A61B 2034/305; A61B 2034/306; A61B 2017/2936; A61B 2017/2939; A61B 2017/2933; A61B 2017/2937; A61B 2017/2947; A61B 2017/2934
See application file for complete search history.

(56) References Cited

U.S. PATENT DOCUMENTS

| | | | |
|---|---|---|---|
| 5,562,701 A | 10/1996 | Huitema et al. | |
| 5,569,299 A | 10/1996 | Dill et al. | |
| 5,710,870 A | 1/1998 | Ohm et al. | |
| 6,019,780 A | 2/2000 | Lombardo et al. | |
| 6,132,441 A | 10/2000 | Grace | |
| 6,206,903 B1 | 3/2001 | Ramans | |
| 6,394,998 B1* | 5/2002 | Wallace | A61B 34/71 606/1 |
| 6,554,844 B2 | 4/2003 | Lee et al. | |
| 6,676,684 B1 | 1/2004 | Morley et al. | |
| 6,840,938 B1 | 1/2005 | Morley et al. | |
| 6,902,560 B1* | 6/2005 | Morley | A61B 17/062 606/1 |
| 6,994,708 B2 | 2/2006 | Manzo | |
| 7,090,689 B2 | 8/2006 | Nagase et al. | |
| 7,101,363 B2 | 9/2006 | Nishizawa et al. | |
| 7,105,000 B2 | 9/2006 | McBrayer | |
| 7,422,592 B2 | 9/2008 | Morley et al. | |
| 7,566,334 B2 | 7/2009 | Christian et al. | |
| 7,608,083 B2 | 10/2009 | Lee et al. | |
| 7,744,608 B2 | 6/2010 | Lee et al. | |
| 7,914,522 B2 | 3/2011 | Morley et al. | |
| 7,935,130 B2* | 5/2011 | Williams | A61B 34/71 606/205 |
| 8,245,594 B2 | 8/2012 | Rogers et al. | |
| 8,262,655 B2 | 9/2012 | Ghabrial et al. | |
| 8,277,443 B2 | 10/2012 | Jinno | |
| 8,333,780 B1 | 12/2012 | Pedros et al. | |
| 8,343,141 B2 | 1/2013 | Madhani et al. | |
| 8,394,120 B2 | 3/2013 | Krzyzanowski | |
| 8,398,619 B2 | 3/2013 | Doyle et al. | |
| 8,398,634 B2 | 3/2013 | Manzo et al. | |
| 8,523,900 B2 | 9/2013 | Jinno et al. | |
| 8,540,748 B2 | 9/2013 | Murphy et al. | |
| 8,568,443 B1 | 10/2013 | Jackman et al. | |
| 8,663,270 B2 | 3/2014 | Donnigan et al. | |
| 8,702,748 B2* | 4/2014 | Kim | A61B 34/72 606/205 |
| 2003/0135204 A1 | 7/2003 | Lee et al. | |
| 2004/0193146 A1 | 9/2004 | Lee et al. | |
| 2005/0165429 A1 | 7/2005 | Douglas et al. | |
| 2005/0240178 A1 | 10/2005 | Morley et al. | |
| 2006/0079890 A1 | 4/2006 | Guerra | |
| 2006/0190034 A1 | 8/2006 | Nishizawa et al. | |
| 2008/0119870 A1 | 5/2008 | Williams | |
| 2010/0016852 A1 | 1/2010 | Manzo et al. | |
| 2010/0076483 A1 | 3/2010 | Imuta | |
| 2010/0185232 A1 | 7/2010 | Hughett, Sr. et al. | |
| 2010/0191251 A1* | 7/2010 | Scott | A61B 18/1445 606/130 |
| 2010/0298638 A1 | 11/2010 | Slater | |
| 2011/0004210 A1 | 1/2011 | Johnson et al. | |
| 2011/0092776 A1 | 4/2011 | Kawai et al. | |
| 2011/0118778 A1 | 5/2011 | Burbank | |
| 2011/0238064 A1 | 9/2011 | Williams | |
| 2011/0251608 A1 | 10/2011 | Timm et al. | |
| 2011/0276049 A1 | 11/2011 | Gerhardt | |
| 2013/0197492 A1 | 8/2013 | Kishi et al. | |
| 2014/0188159 A1* | 7/2014 | Steege | A61B 17/29 606/207 |

FOREIGN PATENT DOCUMENTS

| | | |
|---|---|---|
| WO | 2013-063675 A1 | 5/2013 |
| WO | WO 2013-063675 | 5/2013 |
| WO | 2015-088647 A1 | 6/2015 |

OTHER PUBLICATIONS

International Preliminary Report with International Search Report and Written Opinion issued in PCT/US2015/041341 dated Feb. 14, 2017.
International Search Report and Written Opinion issued in PCT/US2015/041442 dated May 13, 2016.
International Search Report and Written Opinion issued in PCT/US2016/038458 dated Sep. 12, 2016.
Extended European Search Report issued in corresponding European Application No. 15831995.4 dated Mar. 19, 2018.
Extended European Search Report issued in European Application No. 15831402.1 dated Jan. 8, 2018.
Chinese Office Action issued in corresponding Chinese Application No. 201580043422.X dated Nov. 5, 2018.
Australian Examination Report issued in corresponding Australian Application No. 2015302214 dated Mar. 27, 2019, 2 pages.
Australian Examination Report issued in corresponding Australian Application No. 2015302216 dated Mar. 28, 2019, 4 pages.
Office Action issued in corresponding Japanese Appl. No. JP 2017-507394, dated May 29, 2019, together with English language translation (12 pages).
Office Action issued in corresponding Japanese Appl. No. JP 2017-507393 dated May 7, 2019, together with English language translation (8 pages).

* cited by examiner

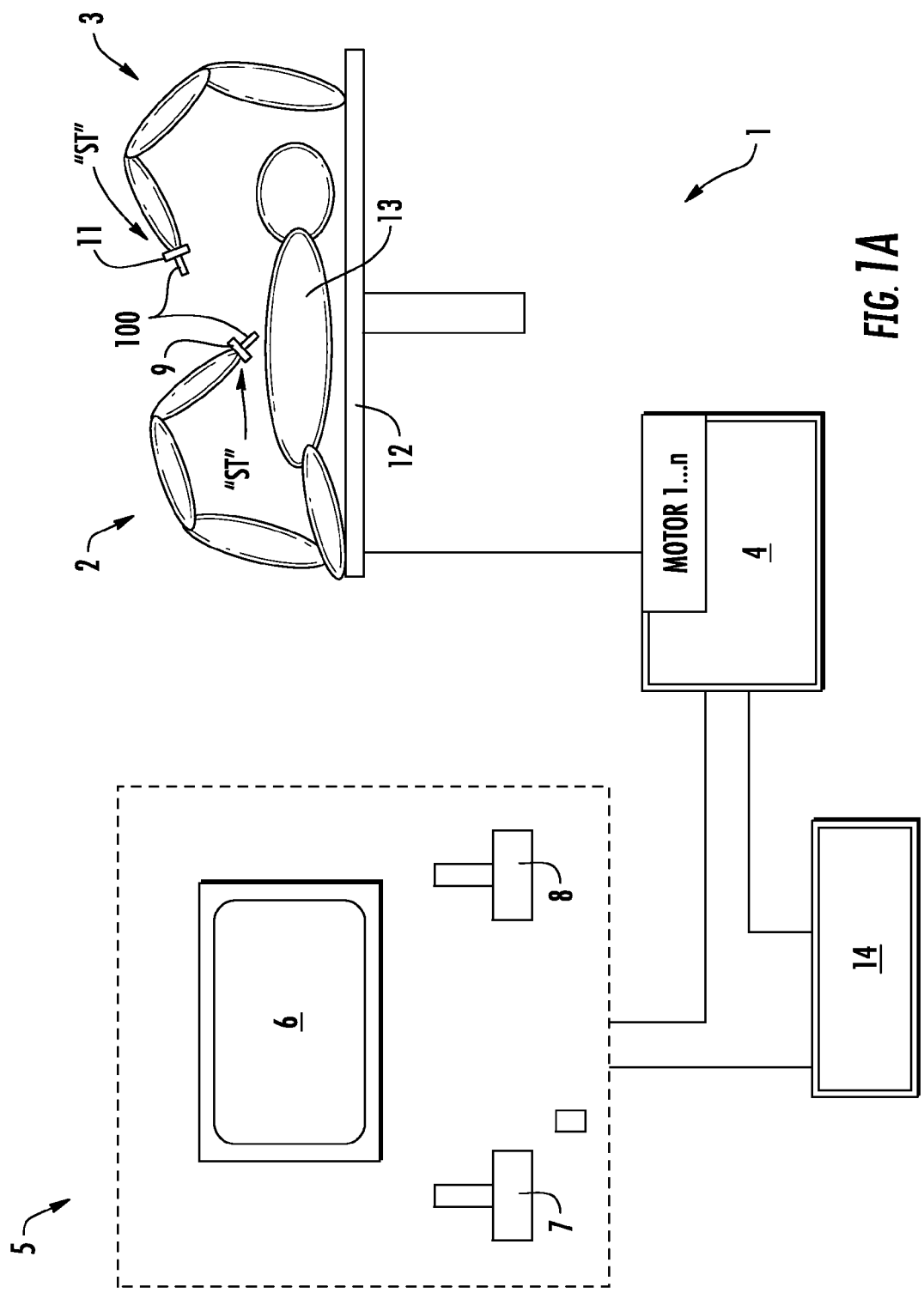

ROBOTICALLY CONTROLLING MECHANICAL ADVANTAGE GRIPPING

CROSS-REFERENCE TO RELATED APPLICATIONS

This application is a U.S. National Stage Application filed under 35 U.S.C. § 371(a) of International Patent Application No. PCT/US2015/041442, filed Jul. 22, 2015, which claims the benefit of and priority to U.S. Provisional Patent Application No. 62/036,904, filed Aug. 13, 2014, the entire disclosure of which is incorporated by reference herein.

TECHNICAL FIELD

The present disclosure relates to robotics, and more specifically to robotic surgical devices and/or systems for performing surgical procedures and methods of use thereof.

BACKGROUND

Robotic surgical systems have been used in minimally invasive medical procedures. Some robotic surgical systems included a console supporting a robot arm, and at least one end effector such as a forceps or a grasping tool that was mounted to the robot arm. During a medical procedure, the end effector was inserted into a small incision (via a cannula) or a natural orifice of a patient to position the end effector at a work site within the body of the patient.

Cables extended from the robot console, through the robot arm, and connected to wrist and/or jaw assemblies of the end effector. In some instances, the cables were actuated by motors that were controlled by a processing system with a user interface for a surgeon or clinician to be able to control the robotic surgical system including the robot arm, the wrist assembly and/or the jaw assembly.

In some instances, the wrist assembly had multiple degrees of freedom for movement of the jaw assembly using several cables. For example, for grasping or cutting end effectors, the wrist assembly provided the freedom for movement by allowing changes to pitch, yaw, or an opening and closing of the jaw assembly.

As demand for smaller end effectors increased, device manufacturers continued to develop end effectors such as grasping and cutting end effectors having smaller cross-sectional areas. These smaller cross-sectional areas reduced the total force that could be applied between the jaws of the end effector. Additionally, designing end effectors supporting multiple degrees of motion required several cables. Each additional cable that was needed further limited the ability to reduce the cross sectional areas of these end effectors.

There is a need for end effectors having small cross-sectional areas that are able to provide higher forces between two jaws of the end effectors while providing multiple degrees of motion.

SUMMARY

An end effector of a surgical tool may include a housing having proximal and distal ends. The housing may define a longitudinal axis that extends through the proximal and distal ends. The end effector may include a jaw support shaft, a pair of jaw members, an articulation member, and a pair of cam pulleys.

The jaw support shaft may define a pivot axis that extends therethrough. The pivot axis can be transverse to the longitudinal axis of the housing. In embodiments, the jaw support shaft may be mounted to the housing.

The pair of jaw members may be supported on the jaw support shaft and may be pivotable about the pivot axis. Each of the pair of jaw members may define an arcuate slot therethrough. Each arcuate slot may be adapted to receive the jaw support shaft. The jaw support shaft may be adapted to slide along the arcuate slots of the pair of jaw members to enable the pair of jaw members to pivot about the pivot axis.

The articulation member may define a slot therethrough. The slot may be adapted to receive the jaw support shaft to support the articulation member between the pair of jaw members. The articulation member may include a pair of articulation pins extending therefrom and coupled to the pair of jaw members. In some embodiments, at least a portion of at least one of the pair of articulation pins can be positioned proximally of the pivot axis. In embodiments, at least a portion of at least one of the pair of articulation pins may be positioned distally of the pivot axis. The articulation member may be rotatable about the jaw support shaft to articulate the pair of jaw members relative to the longitudinal axis. In some embodiments, the pivot axis of the jaw support shaft may be longitudinally offset from the pair of articulation pins.

The pair of articulation pins may be adapted to couple to the pair of jaw members. Each jaw member of the pair of jaw members may define an articulation pin opening adapted to receive one of the pair of articulation pins to couple the articulation member to the pair of jaw members. In some embodiments, the pair of jaw members may be adapted to articulate relative to the longitudinal axis of the housing to a yaw angle of about ninety degrees in response to rotation of the articulation member about the jaw support shaft. The pair of jaw members may be pivotable about the pivot axis while in an articulated position relative to the longitudinal axis.

The pair of cam pulleys may be mounted to the housing and coupled to the pair of jaw members. The pair of cam pulleys may be rotatable about the pivot axis to pivot the pair of jaw members between open and closed conditions. In embodiments, the pair of jaw members may be adapted to pivot to a jaw angle of about sixty degrees in response to rotation of at least one of the pair of cam pulleys.

Each cam pulley of the pair of cam pulleys can be coupled to at least one first cable and the articulation member can be coupled to at least one second cable. The at least one first cable and the at least one second cable may be coupled to at least one motor so that actuation of the at least one motor articulates and/or pivots the pair of jaw members.

In one aspect of the present disclosure, an end effector for use and connection to a robot arm of a robotic surgical system, wherein the end effector may be controlled by at least one cable extending from a motor of a control device of the robot surgical system may be provided.

According to yet another aspect, a method of actuating an end effector of a robotic surgical system may be provided. The method may include rotating a cam pulley secured to a pair of jaw members to open or close the pair of jaw members about a pivot axis; and rotating an articulation member positioned between the pair of jaw members to articulate the pair of jaw members relative to a longitudinal axis of the end effector with a pair of articulation pins that extends from the articulation member, wherein at least one of the pair of articulation pins may be at least partially longitudinally offset from the pivot axis.

According to still another aspect, an end effector of a surgical tool may be provided. The end effector may include a housing, a jaw support shaft, a pair of jaw members, and a pair of cam pulleys.

Each of the pair of jaw members may define a support shaft slot therethrough and may include a pulley pin and a jaw pin extending therefrom. In embodiments, the support shaft slot of each of the pair of jaw members may be curvate. Each of the pair of jaw members may define a jaw pin slot adapted to receive an opposing one of the jaw pins of the pair of jaw members. In embodiments, the jaw pin slot may be curvate.

The pair of cam pulleys may be mounted to the jaw support shaft and coupled to the pair of jaw members. The pair of cam pulleys may be rotatable about the pivot axis to pivot the pair of jaw members about the jaw support shaft. Each of the pair of cam pulleys may include a pulley pin slot. The pulley pin slot may be adapted to receive the pulley pin of a respective one of the pair of jaw members. At least one cable may be secured to the pair of cam pulleys. The at least one cable may be movable to rotate at least one of the pair of cam pulleys to pivot at least one of the pair of jaw members about the pivot axis.

In embodiments, at least one first cable may be coupled to a first one of the pair of cam pulleys and at least one second cable may be coupled to a second one of the pair of cam pulleys. The first one of the pair of cam pulleys and the second one of the pair of cam pulleys may be coupled to at least one motor so that actuation of the at least one motor effectuates at least one of: (1) an articulating movement or (2) a pivoting movement of the pair of jaw members.

In one aspect, an end effector for use and connection to a robot arm of a robotic surgical system may be provided. The end effector may be controlled by at least one cable extending from at least one motor of a control device of the robot surgical system. The end effector may include a housing, a jaw support shaft, a pair of jaw members, and a pair of cam pulleys.

The pair of cam pulleys may be rotatable about the pivot axis to effectuate at least one of: (1) an articulating movement or (2) a pivoting movement of the pair of jaw members about the jaw support shaft.

In embodiments, the at least one cable may include at least one first cable that may be coupled to a first one of the pair of cam pulleys and at least one second cable that may be coupled to a second one of the pair of cam pulleys. The first one of the pair of cam pulleys and the second one of the pair of cam pulleys are coupled to the at least one motor.

Further details and aspects of exemplary embodiments of the present disclosure are described in more detail below with reference to the appended figures.

BRIEF DESCRIPTION OF THE DRAWINGS

The accompanying drawings, which are incorporated in and constitute a part of this specification, illustrate embodiments of the disclosure and, together with a general description of the disclosure given above, and the detailed description of the embodiment(s) given below, serve to explain the principles of the disclosure, wherein:

FIG. 1A is a schematic illustration of a medical work station and operating console in accordance with the present disclosure;

DETAILED DESCRIPTION

Figure 1B:
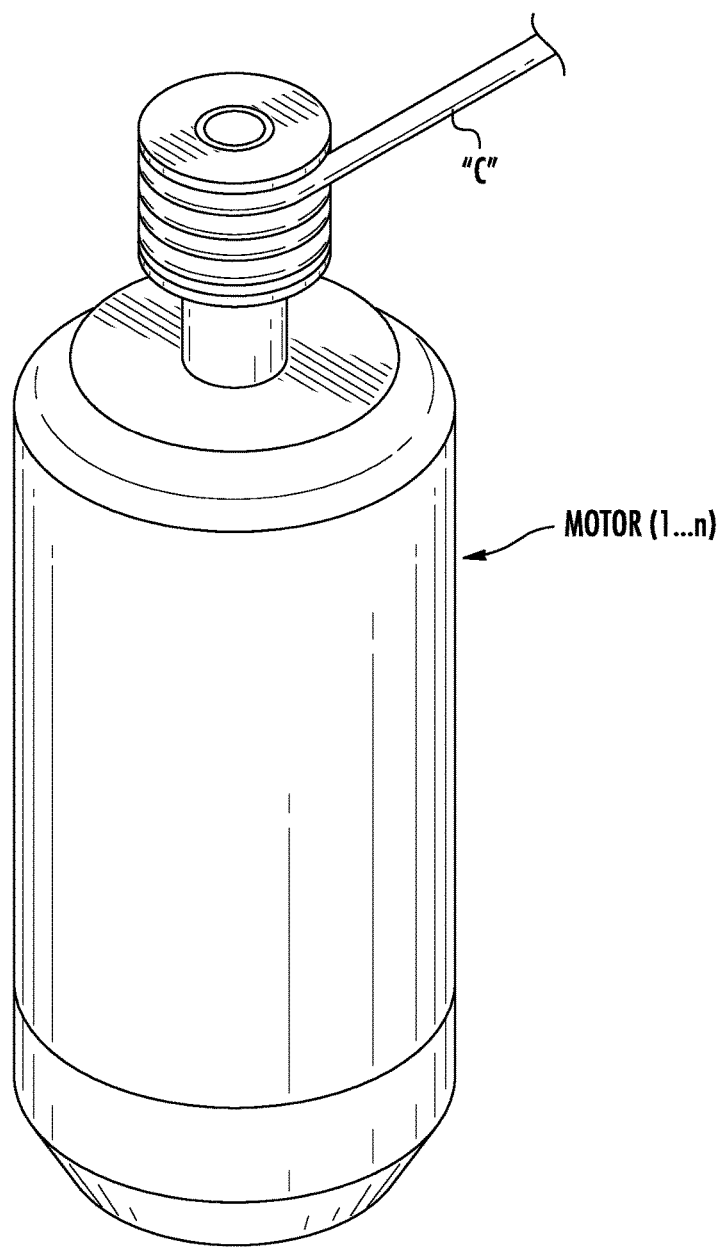
FIG. 1B is a schematic, perspective view of a motor of a control device of the medical work station of FIG. 1A.

Robotically controlled end effectors in accordance with the present disclosure enable cable driven movement of compact jaw assemblies for increased mechanical advantage grasping. The end effectors described herein include an articulation member that provides bilateral articulation of the respective jaw assemblies up to approximately ninety degrees from a longitudinal axis of the end effector. At least one cam pulley of these end effectors can be rotated to position the jaw members thereof in an open condition so that the jaw members define a jaw angle up to approximately sixty degrees.

Embodiments of the presently disclosed end effectors are described in detail with reference to the drawings, in which like reference numerals designate identical or corresponding elements in each of the several views. As used herein the term "distal" refers to that portion of the end effector that is farther from the user, while the term "proximal" refers to that portion of the end effector that is closer to the user.

Referring initially to FIGS. 1A and 1B, a medical work station is shown generally as work station 1 and generally may include a plurality of robot arms 2, 3; a control device 4; and an operating console 5 coupled with control device 4. Operating console 5 may include a display device 6, which may be set up in particular to display three-dimensional images; and manual input devices 7, 8, by means of which a person (not shown), for example a surgeon, may be able to telemanipulate robot arms 2, 3 in a first operating mode, as known in principle to a person skilled in the art.

Each of the robot arms 2, 3 may include a plurality of members, which are connected through joints, and an attaching device 9, 11, to which may be attached, for example, a surgical tool "ST" supporting an end effector 100, in accordance with any one of several embodiments disclosed herein, as will be described in greater detail below.

Robot arms 2, 3 may be driven by electric drives (not shown) that are connected to control device 4. Control device 4 (e.g., a computer) may be set up to activate the drives, in particular by means of a computer program, in such a way that robot arms 2, 3, their attaching devices 9, 11 and thus the surgical tool (including end effector 100) execute a desired movement according to a movement defined by means of manual input devices 7, 8. Control device 4 may also be set up in such a way that it regulates the movement of robot arms 2, 3 and/or of the drives.

Medical work station 1 may be configured for use on a patient 13 lying on a patient table 12 to be treated in a minimally invasive manner by means of end effector 100. Medical work station 1 may also include more than two robot arms 2, 3, the additional robot arms likewise being connected to control device 4 and being telemanipulatable by means of operating console 5. A medical instrument or surgical tool (including an end effector 100) may also be attached to the additional robot arm. Medical work station 1 may include a database 14, in particular coupled to with control device 4, in which are stored, for example, preoperative data from living being 13 and/or anatomical atlases.

For a detailed discussion of the construction and operation of medical work station 1, reference may be made to U.S. Patent Publication No. 2012/0116416, filed on Nov. 3, 2011, entitled "Medical Workstation," the entire contents of which are incorporated herein by reference.

Control device 4 may control a plurality of motors (Motor 1 . . . n) with each motor configured to wind-up or let out a length of a cable "C" (FIG. 1B) extending through each robot arm to end effector 100 of the surgical tool. In use, as cables "C" are wound-up and let out, cables "C" effect operation and/or movement of each end effector 100 of the surgical tool. Control device 4 may coordinate the activation of the various motors (Motor 1 . . . n) to coordinate a winding-up or letting out a length of a respective cable "C" in order to coordinate an operation and/or movement of a respective end effector. Although FIG. 1B shows a single cable "C" that is wound up or let out by a single motor, in some instances two or more cables or two ends of a single cable may be wound up or let out by a single motor. For example, in some instances, two cables or cable ends may be coupled in opposite directions to a single motor so that as the motor may be activated in a first direction, one of the cables winds up while the other cable lets out. Other cable configurations may be used in different embodiments.

Figure 2:
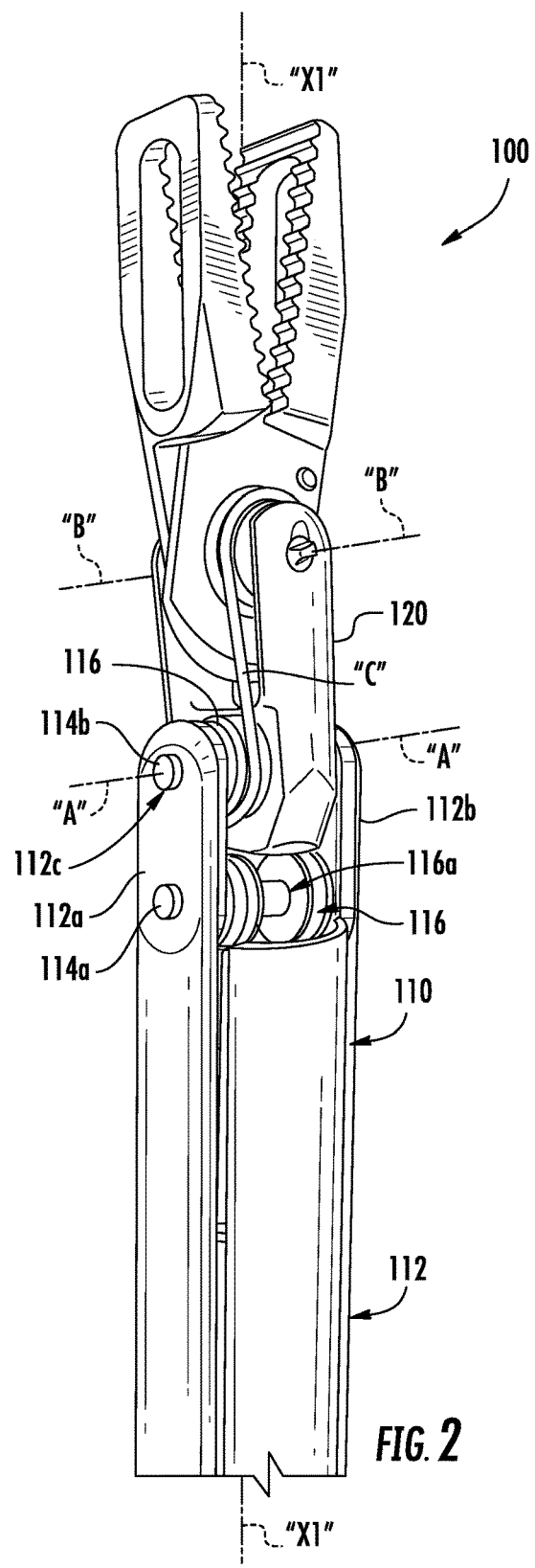
FIG. 2 is a perspective view of an end effector, according to an embodiment of the present disclosure, for use in the medical work station of FIG. 1A, illustrating one embodiment of a jaw assembly thereof in an unarticulated and open condition.

An end effector for connection to robot arms 2, 3 and for manipulation by control device 4, is generally designated as 100. As seen in FIG. 2, end effector 100 may include a wrist assembly 110 and a jaw assembly 120 pivotally connected to wrist assembly 110. Wrist assembly 110 may include a wrist housing 112, in the form of a distally extending clevis, defining a first longitudinal axis "X1-X1." Wrist housing 112 defines a first pivot axis "A-A" that is oriented orthogonal to first longitudinal axis "X1-X1." In an embodiment, first pivot axis "A-A" may extend through first longitudinal axis "X1-X1." Wrist housing 112, being in the form of a clevis, may include a pair of spaced apart, opposed upright supports 112a, 112b through which first pivot axis "A-A" extends. Each of opposed upright supports 112a, 112b defines a plurality of openings 112c.

Wrist assembly 110 further may include a first support shaft 114a and a second support shaft 114b, each of which is secured within, and extends between, a longitudinally aligned pair of the plurality of openings 112c of opposed upright supports 112a, 112b. First support shaft 114a may be disposed at a location along the first longitudinal axis "X1-X1" that may be longitudinally spaced apart from second support shaft 114b. Each of support shaft 114a, 114b supports one or more cam pulleys 116. Each cam pulley 116 defines an opening 116a therethrough that receives one of the first and/or second support shafts 114a, 114b. One or more cam pulleys 116 can be rotatably mounted to, or fixedly secured to, one of first and/or second support shafts 114a, 114b. As can be appreciated, first and/or second support shafts 114a, 114b can support any number of cam pulleys 116 having any suitable shape or dimension.

Figure 3:
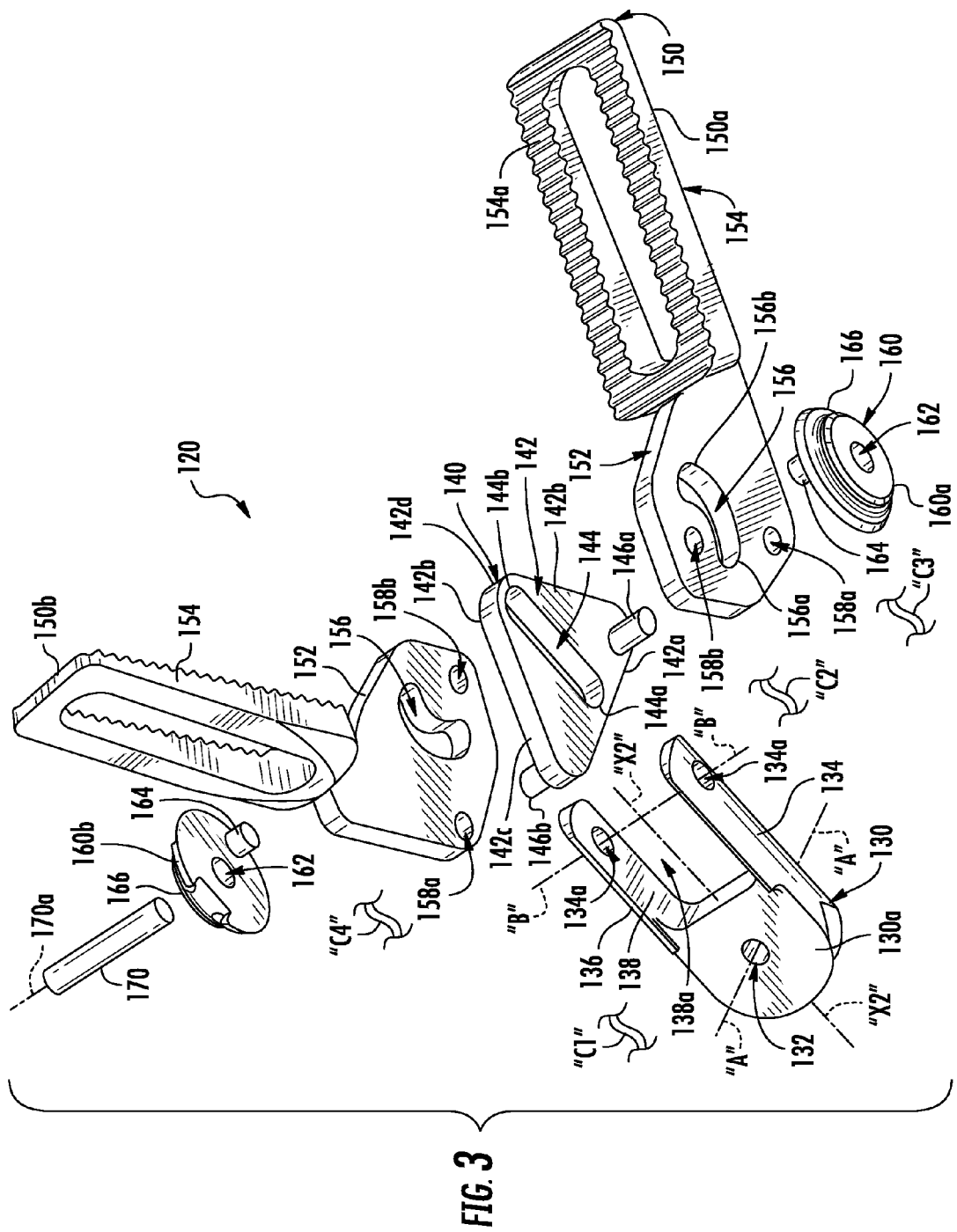
FIG. 3 is a perspective view, with parts separated, of the jaw assembly of FIG. 2.

Turning now to FIG. 3, one embodiment of jaw assembly 120 may include a jaw housing 130, an articulating member 140, a pair of jaw members 150, a pair of cam pulleys 160, and a jaw support shaft 170.

Jaw housing 130, which may be in the form of a clevis, defines a longitudinal axis "X2-X2" that extends therethrough. Jaw housing 130 has a body 130a that defines an opening 132 therethrough adapted and dimensioned to receive second support shaft 114b to pivotally connect jaw assembly 120 to wrist assembly 110. In particular, body 130a may be positionable on second support shaft 114b between a pair of cam pulleys 116. Body 130a may include opposed upright supports 134, 136 that extend distally from body 130a. Opposed upright supports 134, 136 are spaced apart and include inner surfaces therebetween in the form of a saddle 138. The inner surfaces 138 may define a U-shaped opening 138a adapted to receive at least portions of articulating member 140, the pair of jaw members 150, the pair of cam pulleys 160, and jaw support shaft 170. Each of opposed upright supports 134, 136 defines a shaft opening 134a therethrough adapted and dimensioned to receive jaw support shaft 170 to enable support shaft 170 to support articulating member 140, the pair of jaw members 150, and the pair of cam pulleys 160. Shaft openings 134a of opposed upright supports 134, 136 can be longitudinally aligned with one another.

As seen in FIGS. 2 and 3, a second pivot axis "B-B," which extends through opposed upright supports 134, 136 (e.g., through shaft openings 134a), can be oriented orthogonal to the first pivot axis "A-A" and orthogonal to the first longitudinal axis "X1-X1." In some embodiments, the first longitudinal axis "X1-X1" may be parallel with the second longitudinal axis "X2-X2" (e.g., jaw assembly 120 may be in a longitudinally aligned orientation with respect to first longitudinal axis "X1-X1"), and second pivot axis "B-B" extends through first longitudinal axis "X1-X1."

With reference again to FIG. 3, articulation member 140 may be received in U-shaped opening 138a of saddle 138 and may include a body 142 that has a triangular configuration. As can be appreciated, body 142 can have any suitable shape and/or dimension. Body 142 may include a bottom surface 142a, a pair of side surfaces 142b that may be planar, and a top surface 142c that tapers distally to a peak 142d. An elongate slot 144 may be defined through body 142 between the pair of side surfaces 142b. Elongate slot 144 may include a proximal end 144a and a distal end 144b. A pair of articulation pins 146a, 146b extends from the pair of side surfaces 142b at a location adjacent proximal end 144a of elongate slot 144. Each articulation pin 146a, 146b of the pair of articulation pins 146a, 146b may be disposed in mirrored relation with the other of the pair of articulation pins 146a, 146b relative to elongate slot 144. Articulation pin 146a of the pair of articulation pins 146a, 146b can extend laterally outwardly in a direction opposite articulation pin 146b of the pair of articulation pins 146a, 146b. The pair of articulation pins 146a, 146b can be secured on articulation member 140 such that at least a portion of one or both of the pair of articulation pins 146a, 146b remains positioned proximal to a second pivot axis "B-B" (described in greater detail below) of jaw assembly 120 that may be aligned with a central long axis 170a of jaw support shaft 170 while jaw support shaft 170 may be positioned within elongate slot 144, including positions at both proximal and distal ends 144a, 144b of elongate slot 144.

With reference to FIGS. 1A, 1B, 2, and 3, one or more cables "C," using any known fastening technique, may be secured to pulleys 160 to enable rotatable movement of the pulleys 160 in clockwise and/or counterclockwise directions about second pivot axis "B-B" to facilitate bilateral articulation of jaw assembly 120 about wrist assembly 110 relative to first longitudinal axis "X1-X1" (described in greater detail below). For example, a single cable "C" can be at least partially wrapped around (e.g., at least 180 degrees), and/or secured to, a single pulley 160 along channel 166. In some instances, instead of a single cable "C" wrapping around a pulley 160, distal ends of a first pair of cables such as cables "C1" and "C2" can be secured to different sides of a pulley 160 at any suitable location to allow clockwise and counterclockwise rotation of the pulley 160 via the cables. Any of these cables "C," including cables "C1" and "C2" have proximal ends that can extend through robot arm 2 or 3 and which can be operatively associated with a respective first motor and/or at least one second motor (not shown) of control device 4.

Referring again to FIG. 3, the pair of jaw members 150 may include a first jaw member 150a and a second jaw member 150b. Each of the pair of jaw members 150 has a base portion 152 and a jaw portion 154 extending distally from base portion 152. An arcuate slot 156 may be defined through base portion 152 and may be adapted and dimensioned to receive jaw support shaft 170 therethrough. Arcuate slot 156 may be adapted and dimensioned to enable jaw support shaft 170 to slide between proximal and distal ends 156a, 156b of arcuate slot 156 as first and second jaw members 150a, 150b pivot about support shaft 170 relative to second pivot axis "B-B." An articulation pin opening 158a and a cam pin opening 158b are defined through each base portion 152. Jaw portion 154 can include a plurality of teeth 154a on a grasping surface thereof.

The pair of cam pulleys 160 may include a first cam pulley 160a and a second cam pulley 160b, each of which can be substantially disc-shaped. Each of the pair of cam pulleys 160 defines a shaft opening 162 therethrough adapted and dimensioned to receive support shaft 170. A cam pin 164 extends from each of the pair of cam pulleys 160. Each cam pin 164 may be received in one of cam pin openings 158b of the pair of jaw members 150. Each of the pair of cam pulleys 160 defines one or more channels 166 in an outer surface thereof. The one or more channels 166 are adapted and dimensioned to be secured to one or more cables such as cables "C3" and/or "C4" to facilitate rotational movement of cam pulleys 160 and pivoting movement of jaw members 150 between open and closed conditions (described in greater detail below.) As can be appreciated, cables "C3" and "C4" can be wrapped around and/or secured to one of the pair of cam pulleys 160 using any suitable fastening technique such as those described above with respect to cables "C1" and "C2." Similar to cables "C1" and "C2," cables "C3" and "C4" have proximal ends that can extend through robot arm 2 or 3 and which can be operatively associated with a respective first motor and/or at least one second motor (not shown) of control device 4. In addition, any of the presently described cables "C," including cables "C1," "C2," "C3," and "C4," can be at least partially wound around one or more of cam pulleys 116. Cam pulleys 116 can function as cable guides for any of the presently described cables "C."

Figure 4:
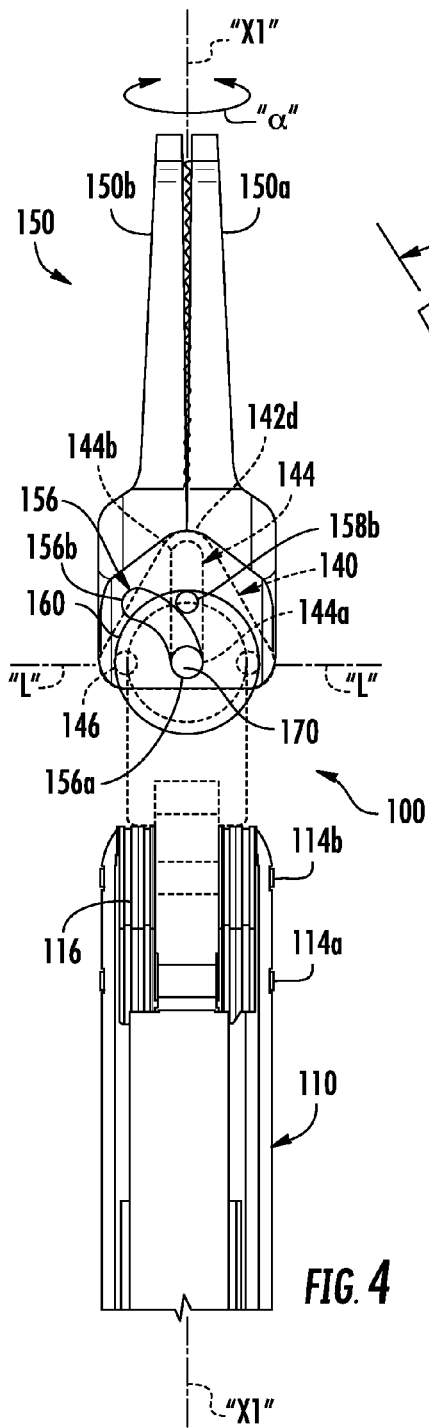
FIG. 4 is a side view of the end effector of FIG. 2 with portions of the jaw assembly removed and/or shown in phantom for clarity, the jaw assembly being illustrated in an unarticulated and closed condition.

In operation, control device 4 can activate one or more electric drives or motors connected thereto to rotate end effector 100 about first longitudinal axis "X1-X1" in either clockwise or counterclockwise directions to any suitable radial orientation (e.g., 360 degrees) as shown by a line designated "α" illustrated in FIG. 4. In order to articulate the pair of jaw members 150 about first pivot axis "A-A," while individual jaw members 150a, 150b are in any radial orientation, the proximal ends of the one or more cables wrapped around one of the pulleys 160a or 160b (e.g. cables "C1" and "C4" or cables "C2" and "C3") may be drawn in a proximal direction while the proximal ends of the other cables wrapped around the other of the pulleys 160b or 160a may be slackened. The direction of articulation about the first pivot axis "A-A" depends on the pulley 160a,b that is selected to have its proximal cable ends drawn in the proximal direction.

Figure 5:
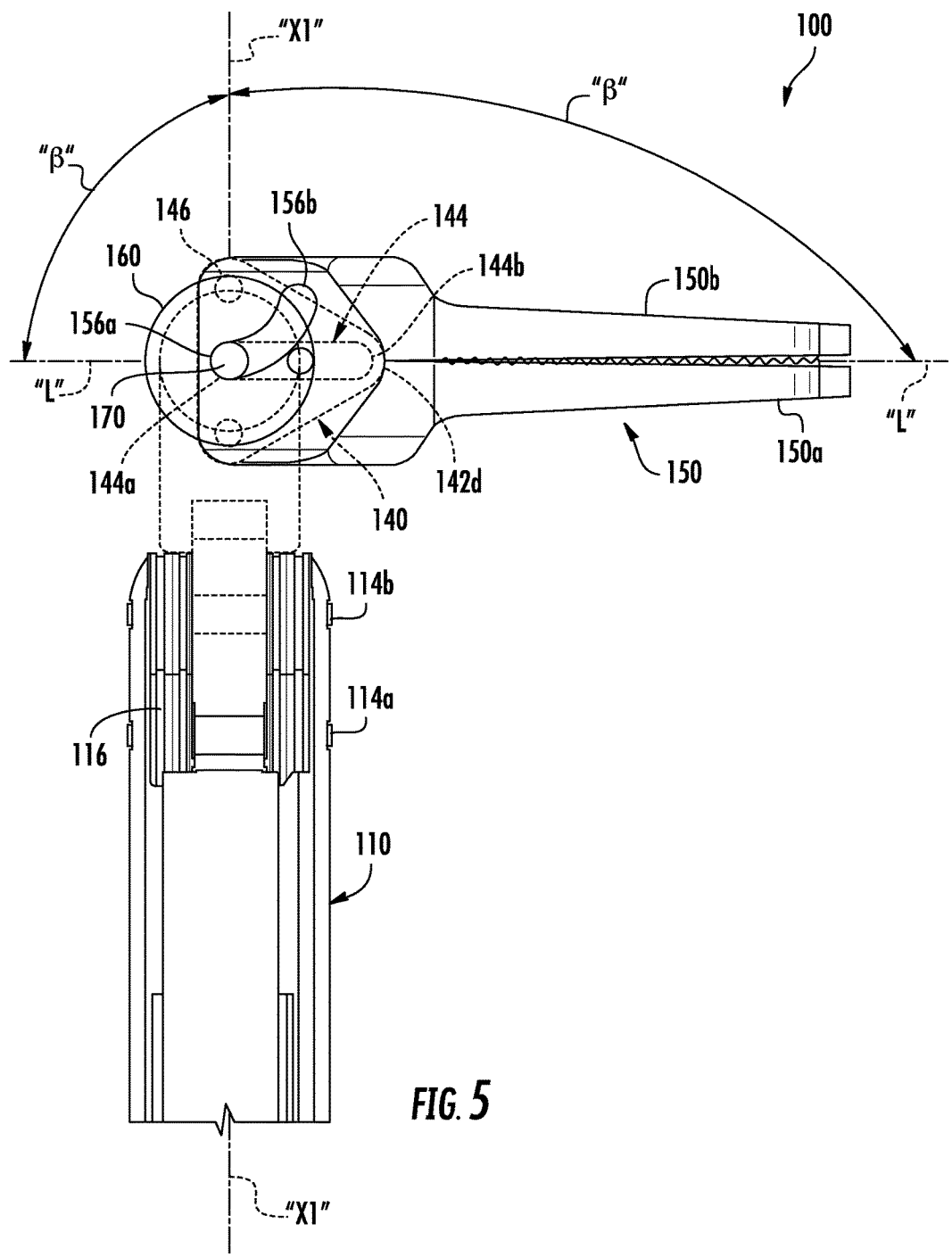
FIG. 5 is a side view of the end effector of FIG. 2 with portions of the jaw assembly removed and/or shown in phantom for clarity, the jaw assembly being illustrated in an articulated and closed condition.

Articulation about pivot axis "B-B" may be achieved by drawing the proximal ends of cables of each respective pulley 160a and 160b that rotate each of the pulleys 160a,b in the same direction (e.g. cables "C1" and "C2" or cables "C3" and "C4"), while letting out the other cable ends. Rotating each of the pulleys 160a,b causes jaw members 150 to rotate via cam pins 164 on the pulleys 160a,b and articulating pins 146 on the articulating member 140 interfacing with respective pin openings 158 on the base portion 152 of jaw members 150. The position of these pins 164 and 146 and pin openings 158 may be changes or altered in different embodiments. For example, pin 164 may be affixed to base member 152 in a different location and a respective pin opening 158 may be provided on the pulley 160. As articulation member 140 pivots, the pair of articulation pins 146, while positioned in articulation pin openings 158a of the pair of jaw members 150, drives the pair of jaw members 150 therewith to articulate the pair of jaw members 150 relative to the first longitudinal axis "X1-X1." In embodiments, the individual jaw members 150a, 150b of the pair of jaw members 150 can be articulated in bilateral directions, namely, two opposed lateral directions. As illustrated by angle "β," depicted in FIG. 5, the pair of jaw members 150 can be articulated in some instances up to a boundary line "L" (e.g., maximum yaw angle), which can be up to about a 90 degree angle relative to the first longitudinal axis "X1-X1" in each of the bilateral directions (e.g., about 180 degrees in total). In embodiments, boundary line "L" can be coplanar with first pivot axis "A-A."

Additionally, in operation, in order to pivot one or both of the pair of jaw members 150 of end effector 100 about second pivot axis "B-B" of jaw assembly 120 between a closed condition (FIG. 4) and an open condition (FIGS. 6 and 7), one of the proximal ends of cables "C3" and "C4" are drawn in a proximal direction as a result of an input from control device 4 to activate a third motor (not shown), and optionally activate a fourth motor (not shown) to let out the other of the proximal ends of cables "C3" and "C4," or vice versa. Depending on which one of the proximal ends of cables "C3" and "C4" are drawn in a proximal direction will determine which direction of pivot, about second pivot axis "B-B," may be transmitted to support cam pulleys 160a, 160b, through cam pins 164, to thus pivot first and second jaw members 150a, 150b.

Figure 6:
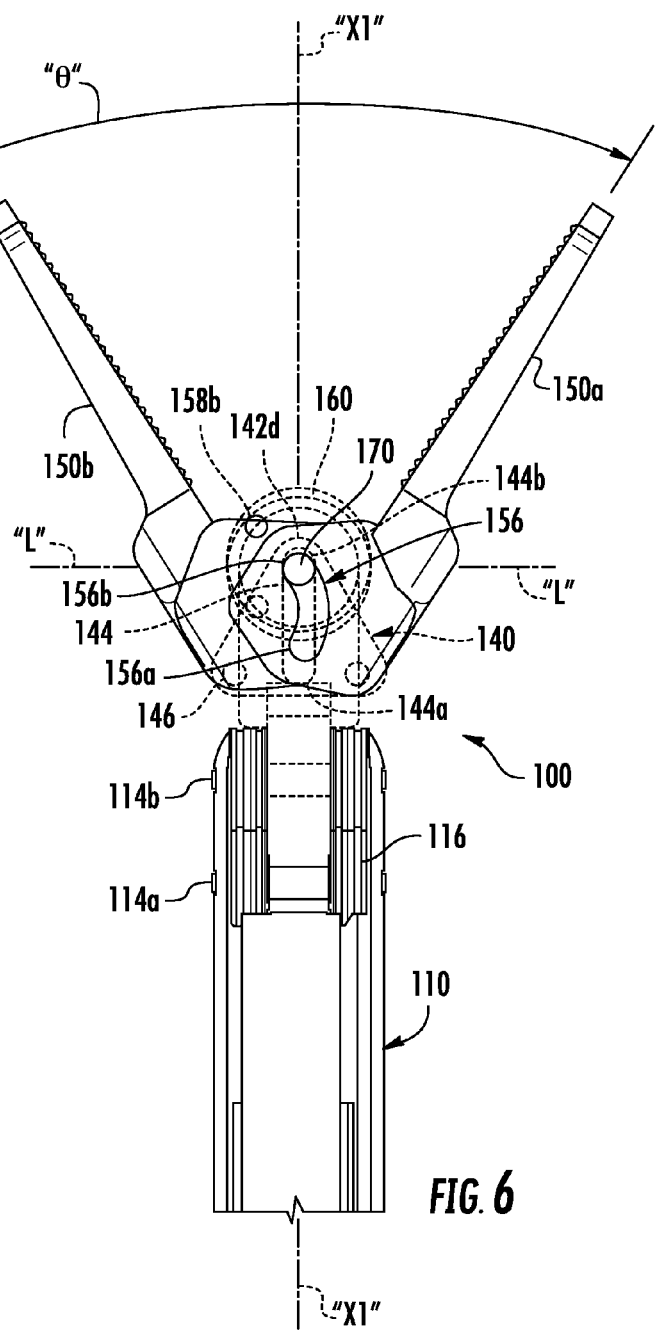
FIG. 6 is a side view of the end effector of FIG. 2 with portions of the jaw assembly removed and/or shown in phantom for clarity, the jaw assembly being illustrated in another unarticulated and open condition.
Figure 7:
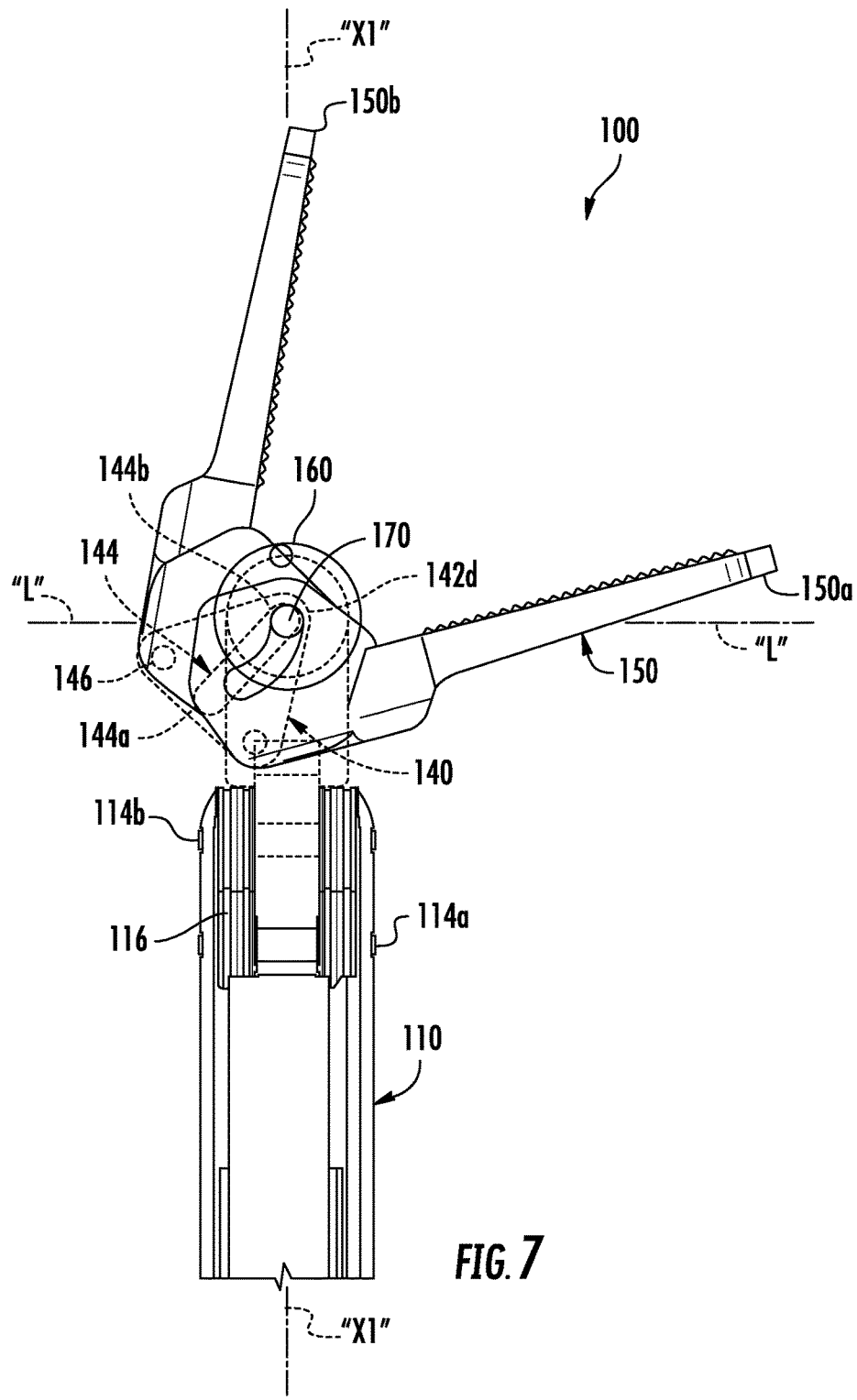
FIG. 7 is a side view of the end effector of FIG. 2 with portions of the jaw assembly removed and/or shown in phantom for clarity, the jaw assembly being illustrated in an articulated and open condition.

In embodiments, first jaw member 150a can be pivoted separate and independent of second jaw member 150b, and vice versa. Additionally, and/or alternatively, first and second jaw members 150a, 150b can be simultaneously pivoted toward and/or away from one another as first and second jaw members 150a, 150b pivot between the closed and open conditions. In embodiments, first and second jaw members 150a, 150b can be pivoted up to a maximum jaw angle "θ" of about 60 degrees, as depicted in FIG. 6. As seen in FIGS. 4, 6, and 7, as first and second jaw members 150a, 150b move between open and closed conditions, articulation member 140 slides along arcuate slot 156 between proximal and distal ends 156a, 156b thereof. For example, in the closed condition (FIG. 4), jaw support shaft 170 may be disposed in proximal end 144a of elongate slot 144 and proximal ends of arcuate slots 156 of the pair of jaw members 150, while in one of the open conditions (FIG. 6 and FIG. 7) jaw support shaft 170 may be disposed in distal end 144b of elongate slot 144 and distal ends of arcuate slots 156 of the pair of jaw members 150. In this regard, pivoting movement of the pair of jaw members 150 to one of the open conditions thereof enables the pair of jaw members 150 and the articulation member 140 to axially translate along first longitudinal axis "X1-X1" in a proximal direction (toward wrist assembly 110) relative to line "L," jaw support shaft 170, and/or the pair of cam pulleys 160, and vice versa with regard to pivoting movement of the pair of jaw members 150 towards the closed condition. As can be appreciated, one or more components of end effector 100 can be simultaneously (and/or separately/independently), rotated, articulated, and/or pivoted.

Figure 8:
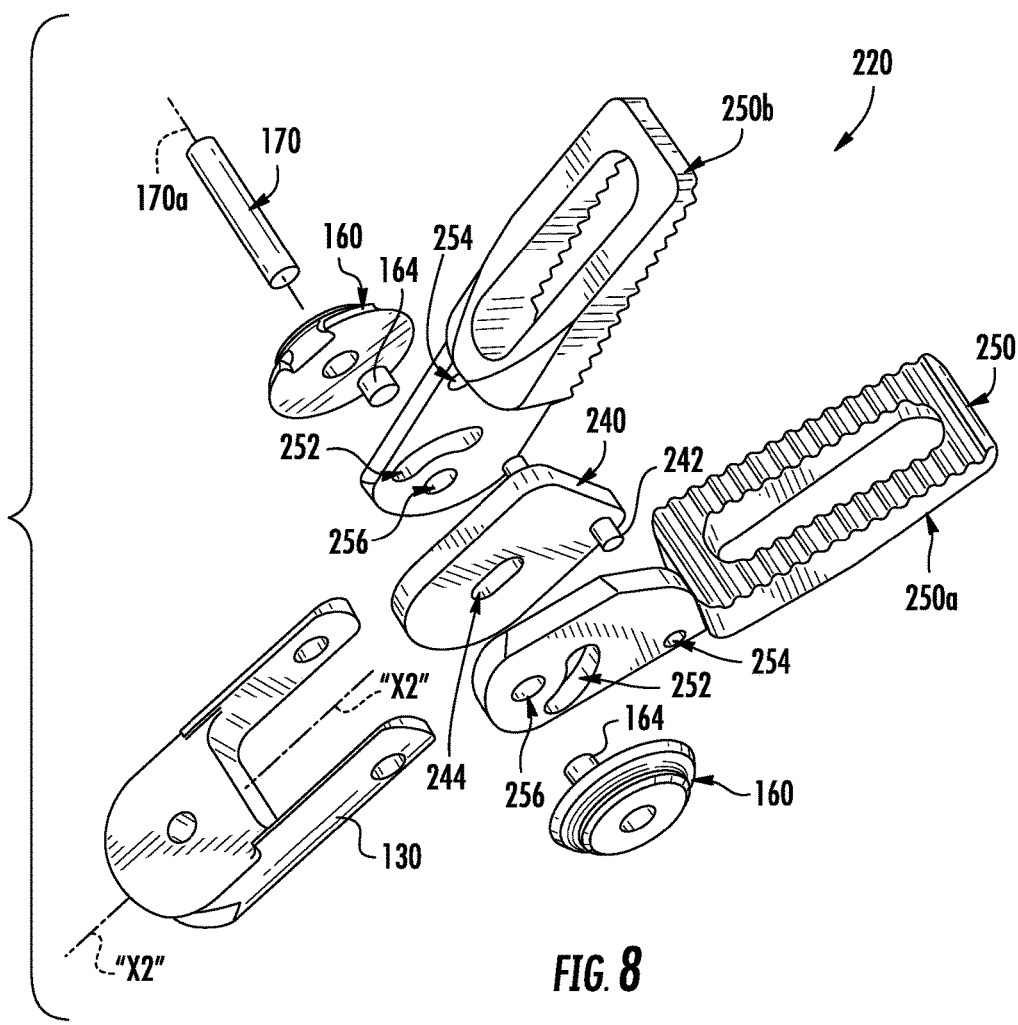
FIG. 8 is a perspective view, with parts separated, of another embodiment of a jaw assembly.

Turning now to FIG. 8, a jaw assembly for connection to an end effector of robot arms 2, 3 and for manipulation by control device 4, in accordance with another embodiment of the present disclosure, is generally designated as 220. Jaw assembly 220 may be substantially similar to jaw assembly 120 and thus will only be described in detail herein to the extent necessary to describe differences in construction and/or operation from those of jaw assembly 120. In particular, jaw assembly 220 may include a jaw housing 130, an articulating member 240, a pair of jaw members 250, a pair of cam pulleys 160, and a jaw support shaft 170.

Articulating member 240 may include a pair of articulating pins 242 extending from opposed side surfaces thereof and defines an elongate slot 244 therethrough adapted and dimensioned to slidably receive jaw support shaft 170. As seen in FIG. 8, each of the pair of articulating pins 242 may be positioned distally of elongate slot 244, and thus, distally of central long axis 170a of jaw support shaft 170, which as described above, may be aligned with second pivot axis "B-B" (see FIG. 2) when coupled to wrist assembly 110.

The pair of jaw members 250 may include a first jaw member 250a and a second jaw member 250b. Each of the pair of jaw members 250 defines an arcuate slot 252 therethrough that may be adapted and dimensioned to receive jaw support shaft 170. Arcuate slot 252 may be adapted and dimensioned to enable jaw support shaft 170 to slide between proximal and distal ends of arcuate slot 252 as first and second jaw members 250a, 250b pivot about support shaft 170 relative to central long axis 170a of support shaft 170 (e.g., and second pivot axis "B-B"—see FIG. 2). An articulation pin opening 254 and a cam pin opening 256 are defined through each of the pair of jaw members 250. Each articulation pin opening 254 may be positioned on one of the pair of jaw members 250 to receive one of articulation pins 242 of articulation member 240 and enable articulation member 240 to articulate the pair of jaw members 250 relative to first longitudinal axis "X1-X1" similar to that described above with respect to articulation member 140. Each cam pin opening 256 may be positioned on one of the pair of jaw members 250 to receive one of cam pins 164 of cam pulleys 160 and enable cam pulleys 160 to pivot the pair of jaw members 250 between open and closed conditions similar to that described above with respect to the pair of jaw members 150.

Figure 9:
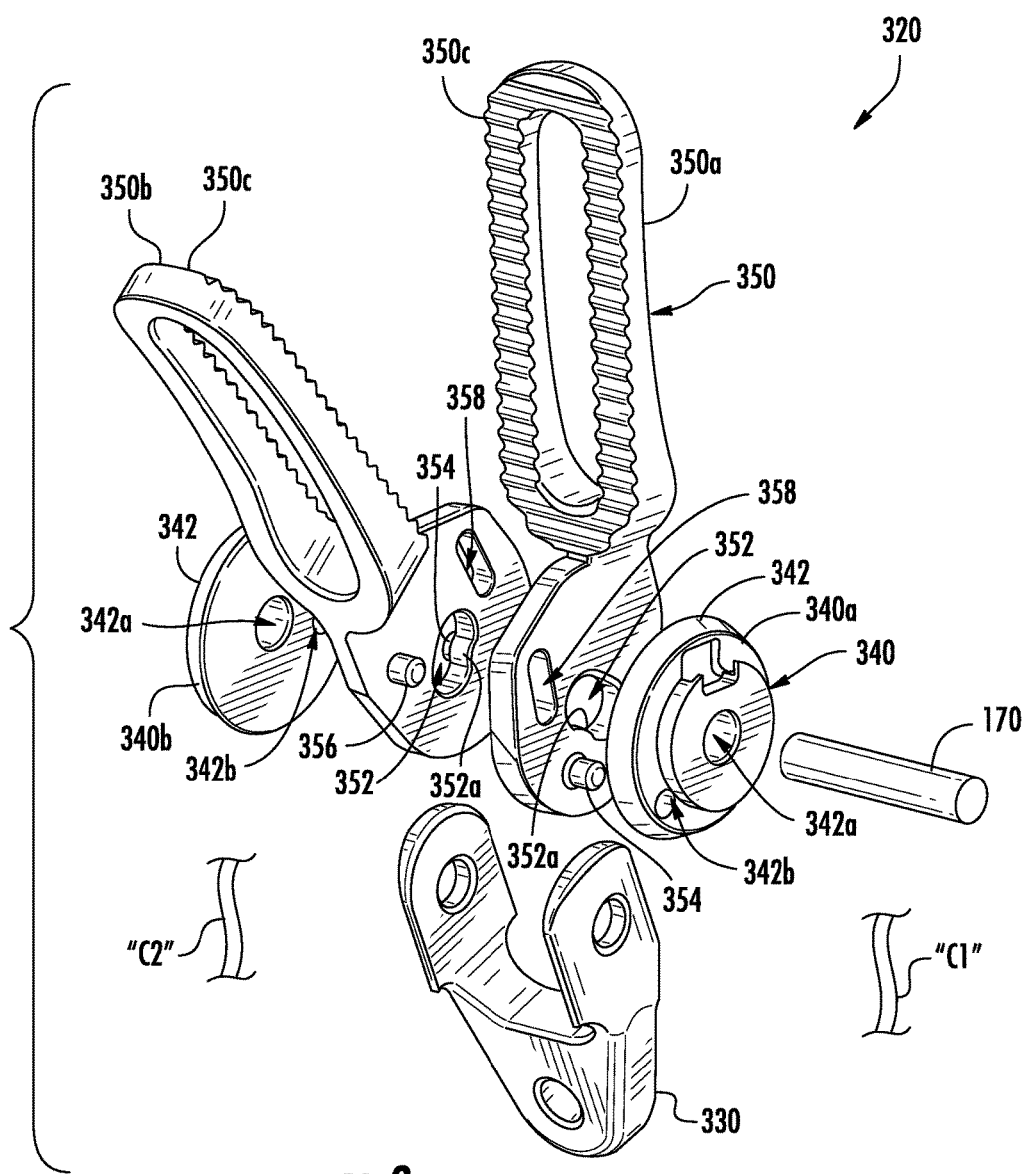
FIG. 9 is a perspective view, with parts separated, of yet another embodiment of a jaw assembly.

Turning now to FIG. 9, a jaw assembly for connection to an end effector of robot arms 2, 3 and for manipulation by control device 4, in accordance with yet another embodiment of the present disclosure, may be generally designated as 320. Jaw assembly 320 may be substantially similar to jaw assemblies 120, 220 and thus will only be described in detail herein to the extent necessary to describe differences in construction and/or operation from those of jaw assemblies 120, 220.

In general, jaw assembly 320 may include a housing 330, a jaw support shaft 170, a pair of cam pulleys 340, and a pair of jaw members 350.

The pair of cam pulleys 340 may include a first cam pulley 340a and a second cam pulley 340b. Each of the pair of cam pulleys 340 may be mounted to the jaw support shaft 170 and has a body 342 defining a central bore 342a and a pulley pin slot 342b. The central bore 342 of each pulley 340 may be adapted to receive the jaw support shaft 170 therethrough. The body 342 of each pulley 340 further defines a cable channel 344 that may be adapted to receive one or more cables therein, which may be at least partially wrapped around, and/or secured to/within, channel 344. For example, a first cable "C1" may be wrapped around first cam pulley 340a and a second cable "C2" may be wrapped around second cam pulley 340b. Instead of a single cable wrapping around a pulley 340, in some instances two separate cables terminating on the pulley 340 may be used instead. The one or more cables may be movable (e.g. via a motor—see FIG. 1B) to rotate or pivot one or both of the pair of cam pulleys 340a, 340b about jaw support shaft 170.

The pair of jaw members 350 may include a first jaw member 350a and a second jaw member 350b. Each of the pair of jaw members 350 defines a support shaft slot 352 through a proximal portion thereof and may include a pulley pin 354 and a jaw pin 356 extending from the proximal portion on opposite side surfaces thereof. The support shaft slot 352 may be adapted and dimensioned to receive jaw support shaft 170 and enable sliding movement of jaw support shaft 170 therein. In embodiments, support shaft slot 352 may be disposed off-center of a center of the proximal portion of one or both of the pair of jaw members 350. The support shaft slot 352 of one or both of the pair of jaw members 350 may be curvate and can include at least one nub 352a. Each of the pair of jaw members 350 defines a jaw pin slot 358 adapted to slidably receive an opposing one of the jaw pins 356 of the pair of jaw members 350. The jaw pin slot 358 can be curvate to provide a non-linear relationship between pulley angle (e.g., a rotational angle of one or both of the pair of pulleys) and jaw angle (e.g., a rotational angle of one or both of the pair of jaw members).

In embodiments, one or more of slots 352 and/or 358 can be shaped to dictate a ratio and motion profile of one or both of the pair of jaw members 150 as one or both of the pair of cam pulleys 350 are actuated. One or more of slots 352 and/or 358 can have any suitable profile (e.g., elongate, circular, elliptical, c-shaped, s-shaped, etc.) to accommodate any suitable relationship (e.g., linear, non-linear) between pulley angle and jaw angle.

In operation, the one or more cables are actuated to rotate one or both of the pair of cam pulleys 340 about jaw support shaft 170 such that jaw pins 356 slide in jaw pin slots 358 and at least one of the jaw members 350b slidingly pivots about jaw support shaft 170 via support shaft slot 352.

Additionally, in operation, movement (e.g., pivoting) of one or both of the pair of cam pulleys 340 imparts pivoting and/or articulating movement of the pair of jaw members 350 about jaw support shaft 170, depending upon the direction of rotation (e.g., clockwise/counterclockwise) and/or amount of rotational displacement of one or both of the pair of the pair of cam pulleys 340. As can be appreciated, the pair of jaw members 350 may be adapted to pivot between open and closed conditions similar to that described above with respect to the pair of jaw members 150. The first and second cam pulleys 340a, 340b can be rotated in the same and/or opposite directions with respect to one another to impart the pivoting and/or articulating movement of the pair of jaw members 350. In embodiments, the first and second cam pulleys 340a, 340b can be rotationally displaced at the same and/or different amounts to impart the pivoting and/or articulating movement of the pair of jaw members 350.

The shape and dimension of support shaft slot 352 may enable the pair of jaw members 350 to slidingly pivot/rotate about jaw support shaft 170 so that the first and second jaw members 350a, 350b approximate one another (e.g., toward the closed condition) in substantially parallel relation. The load distribution along tissue engaging surfaces 350c of the pair of jaw members 350 may vary in part depending on the shape of the support shaft slot 352 and the resultant angle and position of the pair of jaw members 350.

As can be appreciated, any of the presently described jaw assemblies provide increased mechanical advantage with force multiplication features thereof (e.g., pins, slots, cables and/or combinations thereof) for improved grasping. In particular, multiplication of the pulley angle with respect to the jaw angle amplifies force at tips (e.g., distal ends) of the jaw members for an equivalent, or substantially equivalent, tension applied at a proximal end of one or more of the cables. This increased mechanical advantage enables a user to manipulate thick and heavy tissue by generating greater grasping force while minimizing tension in the cables and/or reducing mechanical stress on various components (e.g., cables, pulleys, etc.) of the end effector. In one embodiment, force multiplication features enable the one or both of pair of jaw members to open by 40 degrees when one or more of the pulleys rotate by 80 degrees.

Persons skilled in the art will understand that the structures and methods specifically described herein and shown in the accompanying figures are non-limiting exemplary embodiments, and that the description, disclosure, and figures should be construed merely as exemplary of particular embodiments. The present disclosure is not limited to the precise embodiments described, and that various other changes and modifications may be effected by one skilled in the art without departing from the scope or spirit of the disclosure. Additionally, the elements and features shown or described in connection with certain embodiments may be combined with the elements and features of certain other embodiments without departing from the scope of the present disclosure, and that such modifications and variations are also included within the scope of the present disclosure. Accordingly, the subject matter of the present disclosure is not limited by what has been particularly shown and described.

What is claimed is:

1. An end effector of a surgical tool, the end effector comprising:
    a housing having proximal and distal ends, the housing defining a longitudinal axis that extends through the proximal and distal ends;
    a jaw support shaft mounted to the housing and defining a pivot axis that extends therethrough;
    a pair of jaw members supported on the jaw support shaft and being pivotable about the pivot axis, each of the pair of jaw members defining a support shaft slot therethrough and including a pulley pin and a jaw pin extending therefrom, each of the pair of jaw members defining a jaw pin slot adapted to receive an opposing one of the jaw pins of the pair of jaw members; and
    a pair of cam pulleys mounted to the jaw support shaft and coupled to the pair of jaw members, the pair of cam pulleys being rotatable about the pivot axis to pivot the pair of jaw members about the jaw support shaft, the pair of cam pulleys movable relative to the pair of jaw members.

2. The end effector of claim 1, wherein the jaw pin slot is curvate.

3. The end effector of claim 1, wherein the support shaft slot of each of the pair of jaw members is curvate.

4. The end effector of claim 1, wherein each of the pair of cam pulleys includes a pulley pin slot, the pulley pin slot adapted to receive the pulley pin of a respective one of the pair of jaw members.

5. The end effector of claim 1, wherein at least one cable is secured to the pair of cam pulleys, the at least one cable being movable to rotate at least one of the pair of cam pulleys to pivot at least one of the pair of jaw members about the pivot axis.

6. The end effector of claim 1, wherein at least one first cable is coupled to a first one of the pair of cam pulleys and at least one second cable is coupled to a second one of the pair of cam pulleys, the first one of the pair of cam pulleys and the second one of the pair of cam pulleys being coupled to at least one motor so that actuation of the at least one motor effectuates at least one of: (1) an articulating movement or (2) a pivoting movement of the pair of jaw members.

7. The end effector of claim 1, wherein the pivot axis is transverse to the longitudinal axis.

8. The end effector of claim 1, wherein the pulley pin and the jaw pin of each respective jaw member extend in opposite directions from the respective jaw member.

9. The end effector of claim 1, wherein the pair of jaw members is supported between the pair of cam pulleys.

10. An end effector for use and connection to a robot arm of a robotic surgical system, wherein the end effector is controlled by at least one cable extending from at least one motor of a control device of the robot surgical system, the end effector comprising:
    a housing having proximal and distal ends, the housing defining a longitudinal axis that extends through the proximal and distal ends;
    a jaw support shaft mounted to the housing and defining a pivot axis that extends therethrough;
    a pair of jaw members supported on the jaw support shaft and being pivotable about the pivot axis, each of the pair of jaw members defining a support shaft slot therethrough and including a pulley pin and a jaw pin extending therefrom, each of the pair of jaw members defining a jaw pin slot adapted to receive an opposing one of the jaw pins of the pair of jaw members; and
    a pair of cam pulleys mounted to the jaw support shaft and coupled to the pair of jaw members, the pair of jaw members movable relative to the pair of cam pulleys, the pair of cam pulleys being rotatable about the pivot axis to effectuate at least one of: (1) an articulating movement or (2) a pivoting movement of the pair of jaw members about the jaw support shaft.

11. The end effector of claim 10, wherein the jaw pin slot is curvate.

12. The end effector of claim 10, wherein the support shaft slot of each of the pair of jaw members is curvate.

13. The end effector of claim 10, wherein each of the pair of cam pulleys includes a pulley pin slot, the pulley pin slot adapted to receive the pulley pin of a respective one of the pair of jaw members.

14. The end effector of claim 10, wherein the at least one cable is secured to the pair of cam pulleys, the at least one cable being movable to rotate at least one of the pair of cam pulleys to pivot at least one of the pair of jaw members about the pivot axis.

15. The end effector of claim 10, wherein the at least one cable includes at least one first cable that is coupled to a first one of the pair of cam pulleys and at least one second cable that is coupled to a second one of the pair of cam pulleys, the first one of the pair of cam pulleys and the second one of the pair of cam pulleys being coupled to the at least one motor.

16. The end effector of claim 10, wherein the pivot axis is transverse to the longitudinal axis.

17. The end effector of claim 10, wherein the pulley pin and the jaw pin of each respective jaw member extend in opposite directions from the respective jaw member.

18. A method of actuating an end effector of a robotic surgical system, comprising:

rotating about a pivot axis at least one cam pulley coupled to at least one jaw member by a pulley pin extending therebetween, moving the at least one jaw member relative to the at least one cam pulley; and moving the at least one jaw member about the pivot axis between an open and a closed position with at least one other jaw member, each of the jaw members having a jaw pin and a jaw pin slot adapted to receive the jaw pin from another of the jaw members.

19. The method of claim 18, further comprising:

rotating at least two cam pulleys about the pivot axis, a first of the cam pulleys coupled to a first jaw member, the first jaw member having a jaw pin extending into a jaw pin slot of a second jaw member, a second of the cam pulleys coupled to the second jaw member.

20. The method of claim 18, further comprising rotating the at least one cam pulley about an exterior surface of the at least one jaw member.

* * * * *